United States Patent [19]

Novak et al.

[11] 4,259,585
[45] Mar. 31, 1981

[54] X-RAY EXAMINATION APPARATUS

[75] Inventors: Robert Novak, Amorvägen 8, 18146 Lidingö, Sweden; Kjell Ytterfalk, Spanga, Sweden

[73] Assignee: Robert Novak, Lidingö, Sweden

[21] Appl. No.: 961,732

[22] Filed: Nov. 17, 1978

[30] Foreign Application Priority Data

Nov. 28, 1977 [SE] Sweden .................. 2753047

[51] Int. Cl.³ .................. G01N 21/00; G01N 23/00; H01J 37/20
[52] U.S. Cl. .................. 250/456; 250/439 R
[58] Field of Search .......... 250/439 R, 444, 446 R, 250/446, 447, 448, 449, 450, 451, 456, 476

[56] References Cited

U.S. PATENT DOCUMENTS

| | | | |
|---|---|---|---|
| 1,904,234 | 4/1933 | Haskin et al. | 250/476 |
| 3,577,160 | 5/1971 | White | 250/451 |
| 3,824,397 | 7/1974 | Bauer et al. | 250/444 |
| 4,090,084 | 5/1978 | Epstein | 250/439 |
| 4,146,793 | 3/1979 | Borgstrom et al. | 250/444 |

OTHER PUBLICATIONS

"The American Journal of Roentgenology", 1974, vol. 121, No. 4, pp. 843-845.
Siemens Brochure "Mammomat".

Primary Examiner—Alfred E. Smith
Assistant Examiner—Thomas P. O'Hare
Attorney, Agent, or Firm—Hill, Van Santen, Steadman, Chiara & Simpson

[57] ABSTRACT

In the illustrated embodiment, a compression plate is support-mounted parallel to the breast support plate, and is adjustable relative to the breast support plate for the purpose of adjusting its spatial interval from the breast support plate. The compression plate has a cut-out section (12) of such a size that a larger portion of the breast is left exposed. At the margin of the cut-out section there is a marking (13, 14), reproducible on an X-ray film, for the purpose of locating a specific point in the cut-out section.

11 Claims, 4 Drawing Figures

X-RAY EXAMINATION APPARATUS

BACKGROUND OF THE INVENTION

The invention relates to an X-ray examination apparatus for the female breast comprising an X-ray source supplied by an X-ray generator and a breast support plate on which an X-ray film cassette can be mounted, wherein a compression plate is mounted parallel to the breast support plate between the X-ray source and the breast support plate which compression plate is adjustable in relation to the breast support plate for the purpose of adjusting its distance from the breast support plate.

An X-ray examination apparatus of this type is known from the brochure "Mammomat" of the Siemens Firm. The compression plate is formed here by the side—facing the breast support plate—of a compression cone. If a tumor is discovered after taking a breast photograph of a patient, a tissue specimen must be taken from the tumor. To this end, for a photograph, it is known to press the breast between the support plate and a compression plate provided with small holes over its entire surface ("The American Journal of Roentgenology", 1974, Vol. 121, No. 4, Pages 843–45). The holes of the compression plate are weakly recorded on the X-ray photograph in the form of rings. If the tumor on the photograph is disposed precisely in such a ring, the physician can locate the corresponding hole on the plate and conduct, by means of a biopsy needle, through the hole, a puncture of the breast of the patient who is still in the X-ray examination apparatus, in order, in this manner, to take the tissue specimen. The disadvantage of utilizing such a compression plate consists in that the tumor in a photograph can also be disposed between two holes, so that the photograph must be repeated and, to this end, the plate must be moved relative to the breast, which is consuming and inconvenient for the patient. In addition, bleedings often occur during puncturing which can reach the compression plate. In the case of a repeated use of this plate with other female patients, illnesses such as, for example, viral hepatitis can be communicated. A further disadvantage of the known compression plate consisting of plexiglass is that it impairs the image quality due to secondary radiation.

SUMMARY OF THE INVENTION

The object underlying the invention consists in producing an X-ray examination apparatus comprising a compression plate of the type initially cited within the image quality of the X-ray photograph is not impaired in an undesired manner due to stray radiation, and wherein, within a wide range, access to random locations of the breast is possible, so that, as a rule, one single X-ray photograph suffices for the purpose of determining that particular location in the breast where tissue is to be removed. In addition, contamination of the compression plate due to bleeding is to be largely eliminated.

In accordance with the invention, this object is achieved by virtue of the fact that the compression plate manifests an open section of such a size that a larger portion of the breast is left exposed and that a marking for the purpose of locating a specified point in the section is arranged at the margin of the open section, said marking being reproducible on an X-ray film. Through the area of the open section, the portion of the breast to be photographed is exposed, so that the X-ray image is not impaired by stray radiation in the area of diagnostic relevance. If a breast photograph is first made with a compression plate without an opening, the breast can subsequently be placed for the second photograph with the compression plate provided with an opening such that the puncture-location to be located is with certainty disposed behind the opening, and is accessible for tissue removal through the opening. The puncture location can readily be found by the marking, forming a coordinate system, which is also reproduced in the X-ray image. In addition, it is possible to dry-off the blood from the puncture location before it contaminates the compression plate.

In an advantageous embodiment of the invention, it is proposed that the compression plate, in the marginal region of its cut-out section be reinforced in its thickness on its side facing the breast support plate. What is achieved thereby is that the skin of the breast in the cut-out section is taut, which renders possible a precise puncturing.

A particularly expedient further development of the invention consists in that there is mounted on the housing of the X-ray source a light beam localizer (or indicator) arrangement whose light beam, directed at the compression plate, is adjustable by adjustment means. This makes it possible for the puncture location to be precisely set by means of a light-mark.

The invention shall be explained in further detail in the following on the basis of a sample embodiment illustrated in the drawings; and other objects, features and advantages will be apparent from this detailed disclosure.

DETAILED DESCRIPTION

Figure 1:
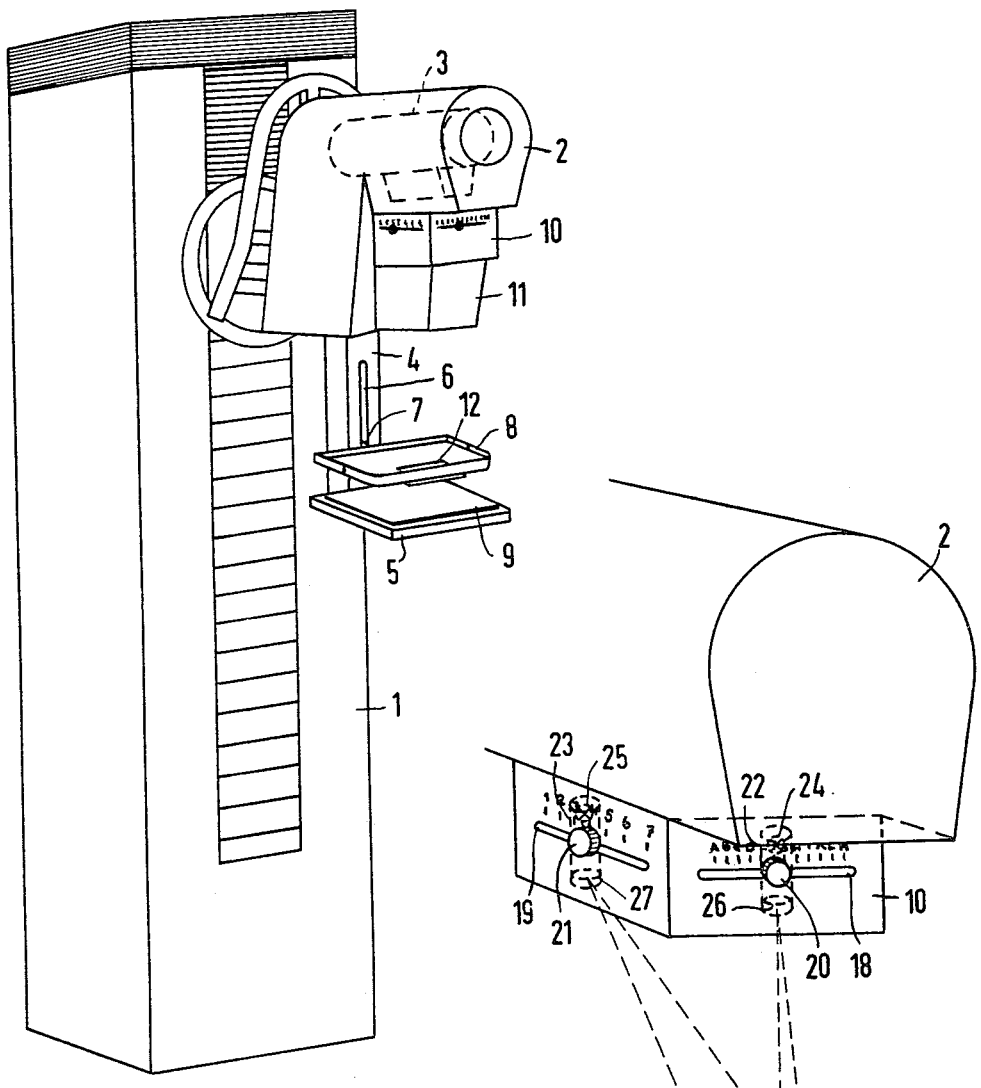
FIG. 1 illustrates an X-ray examination apparatus in accordance with the invention.

FIG. 1 illustrates an X-ray examination apparatus comprising a cabinet 1, and comprising an X-ray tube housing 2 mounted onto the cabinet 1, in which an X-ray tube 3 is arranged. On housing 2, a column 4 is secured which extends in a downward direction and has at a lower free end a photographic plate 5 for mounting a non-illustrated film cassette. On column 4, there is a longitudinal slot 6 from which a pin 7 projects, onto which a compression plate 8 can be mounted in such a manner that it is disposed parallel to the photographic plate 5. Between the photographic plate 5 and compression plate 8, a breast support plate 9 consisting of carbon-fiber-material is arranged. The compression plate 8 can be adjusted by a motor along slot 6 and relative to the breast support plate 9 for the purpose of adjusting its distance from the breast support plate 9.

In addition, a light beam localizer housing 10, projecting downward, is mounted onto X-ray tube housing 2. In the housing 10 a light beam localizer, to be described in greater detail later, is secured, the light beam of which, directed at the compression plate 8, being adjustable by adjustment means. A removable collimator tube 11 is connected to the light beam localizer housing 10 for the purpose of restricting the X-ray beam. The X-ray tube housing 2 with parts 3 through 11 can be adjusted in its height relative to the cabinet 7 located on the floor for the purpose of adjustment in relation to the size of the patient.

Figure 2:
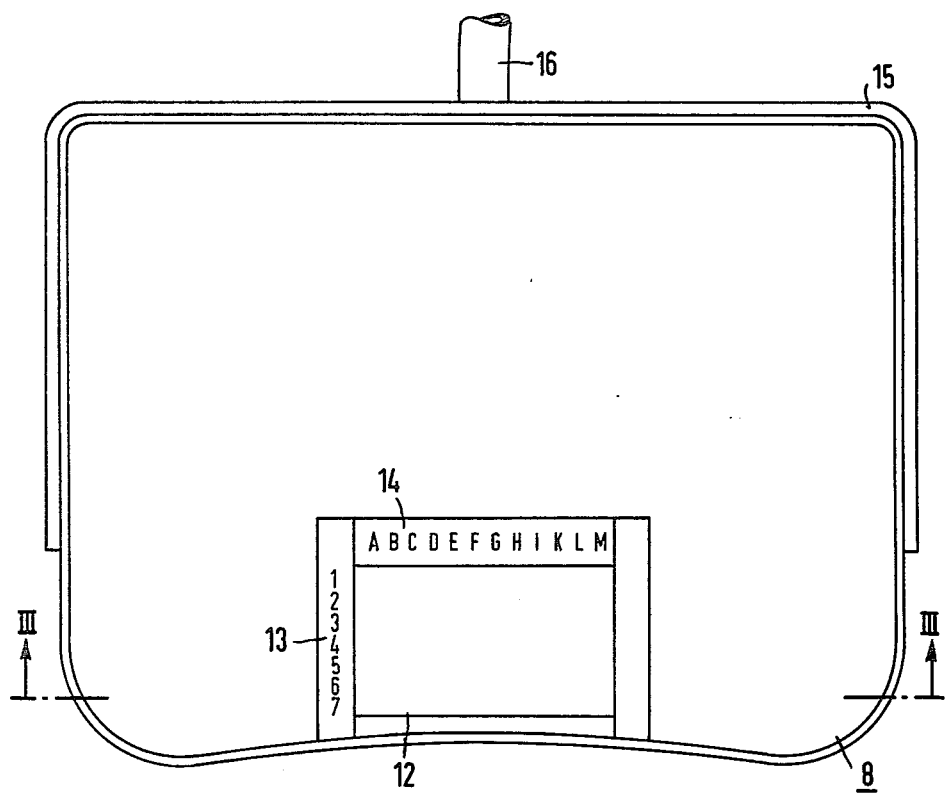
FIG. 2 illustrates the compression plate of the X-ray examination apparatus according to FIG. 1, from above.

FIG. 2 illustrates a compression plate 8 with a rectangular cut-out section 12 which is disposed at the edge of the compression plate and is disposed in the center of the side facing the patient. The cut-out section 12 manifests such a size that a greater portion of the breast is left exposed, and preferably has a size of approximately 40×65 mm. At the margin of the cut-out section 12, radiopaque or radiation-attenuating scales or markings 13, 14, are arranged, which form an orthogonal coordinate system and which serve the purpose of locating a specified point in cut-out section 12. Scale 14 manifests uniformly spaced letters, and scale 13 comprises uniformly spaced digits. The compression plate 8 is supported on a metal bracket 15 which is capable of connection via a tubular piece 16 with pin 7.

Figure 3:
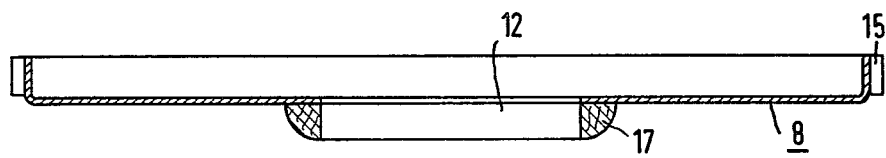
FIG. 3 illustrates a section through the compression plate according to FIG. 2 taken generally along the line III—III.

FIG. 3 illustrates that the compression plate 8 is increased in its thickness in the marginal region of its cut-out section 12 on its side facing the breast support plate 9. The increase in thickness is preferably formed by a wood frame 17 which is rounded off at the corners, in order to avoid secondary radiation due to the thickness increase. The thickness increase amounts to approximately 1.5 cm. The wood frame 17 effects an optimum local compression when it is pressed on the breast and thereby tautens the skin. The friction between the breast and the compression plate 8 is sufficiently great that the breast will not move out of position during the examination.

Figure 4:
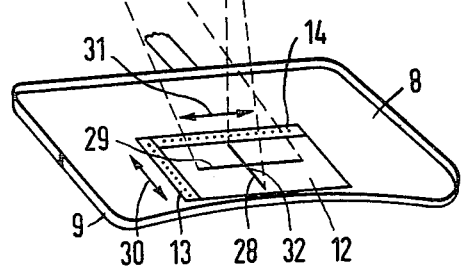
FIG. 4 shows a schematically represented light beam localizer for the X-ray examination apparatus according to FIG. 1.

FIG. 4 illustrates the light beam localizer housing 10 which is mounted onto the X-ray tube housing 2. In housing 10, two light beam localizers 22, 23, are arranged, which, by means of non-illustrated guide means, are adjustable in parallax-free fashion along slots 18, 19, by means of adjustment knobs 20, 21, in the coordinate system formed by the scales 13, 14. Each light beam localizer 22, 23, manifests a light source 24, 25, an optical lens system 26, 27, and an aperture for the formation of light-lines. By displacing the light beam localizer 23 by means of adjusting knob 21 in slot 19, line 29 is adjustable along the digit-coordinate of the scale 13 (arrow 30). By displacing light beam localizer 22 by means of adjustment knob 20 in slot 18, line 28 is adjustable along the letter-coordinates of scale 14 (arrow 31).

During examination, following a panoramic photograph with a compression plate without a cut-out opening, the breast of the patient is pressed between the breast support plate 9 and the compression plate 8, and, on the basis of the first X-ray image, positioned such that the tumor to be examined is disposed in the section 12 of the compression plate 8. Subsequently, an X-ray photograph is made, and the film developed, while the breast of the patient remains pressed between the two plates. The film cassette, disposed between the support plate 5 and the breast support plate 9, can be laterally withdrawn for the purpose of film development without having to change the position of the breast. The tumor can now be readily seen on the developed film, since this portion of the breast is disposed in the cut-out opening 12 of plate 8. The scales 13, 14, are also clearly recognizable on the film. The physician now measures, with a scale, the particular coordinates of the point at which the tumor is disposed. Then, by means of light-lines 28, 29, of the adjustable light beam localizers 22, 23, according to FIG. 4, the corresponding coordinate point 32 on the breast is precisely set. In order to simplify the adjustment, scales can also be arranged on the light beam localizer housing 10 along slots 18, 19, which scales correspond to the scales 13, 14, on the compression plate. Before the physician punctures the breast with the biopsy needle at coordinate point 32 in order to remove a tissue specimen, the collimator tube 11 can be removed in order that there will be sufficient room for the biopsy needle. In FIG. 4, the tube 11 has been removed.

It will be apparent that many modifications and variations may be effected without departing from the scope of the novel teachings and concepts of the present invention.

We claim as our invention:

1. X-ray examination apparatus for the female breast comprising an X-ray source and a breast support plate onto which an X-ray film cassette can be mounted, wherein a compression plate is mounted parallel to the breast support plate between the X-ray source and the breast support plate which compression plate is adjustable relative to the breast support plate for the purpose of adjusting its distance from the breast support plate, wherein the improvement comprises the compression plate (8) having an open section (12) of such a size that a substantial portion of the breast is left exposed, and a marking (13,14) being arranged at the margin of the open section, reproducible on an X-ray film, for the purpose of locating a specified point in the open section, said open section comprising an opening completely through the compression plate and having dimensions in the plane of said compression plate which are substantially greater than the depth of said opening, such dimensions being such as to accommodate the application of a biopsy needle through said opening at any of a series of locations over a substantial area of said opening as identified by said marking, whereby the opening need not be precisely aligned during the application of the compression plate for the fixation of the region of the breast under examination, and whereby subsequent to such fixation, the markings reproduced on the film will serve to identify the particular point over the area of said opening at which the biopsy needle is to be applied, the region above and below said opening being entirely unobstructed to provide for the application of a biopsy needle directly to the tissue framed by the opening without any interposed material.

2. X-ray examination apparatus according to claim 1, characterized in that the open section (12) is rectangular, and that the marking (13, 14) forms an orthogonal coordinate system.

3. X-ray examination apparatus according to claim 1, characterized in that the compression plate (8) is increased in its thickness at the marginal region of its open section (12) on its side facing the breast support plate (9).

4. X-ray examination apparatus according to claim 3, characterized in that the increase in thickness (17) amounts to approximately 1.5 cm.

5. X-ray examination apparatus according to claim 3, characterized in that the increase in thickness (17) is formed by a wood frame.

6. X-ray examination apparatus according to claim 1, characterized in that there is mounted with the X-ray source (3) a light beam localizer arrangement (22, 23) whose light beam, directed at the compression plate (8), is adjustable by adjustment means (20, 21).

7. X-ray examination apparatus according to claim 6, characterized in that there is allocated to the adjustment means (20, 21) a scale-arrangement which corresponds to the marking (13, 14) on the compression plate (8).

8. X-ray examination apparatus according to claim 6, characterized in that a removable tube (11) for the purpose of restricting the radiation path is connected to the light beam localizer (22, 23).

9. X-ray examination apparatus according to claim 1, characterized in that the open section (12) is at the edge of the compression plate (8) and is disposed in the center on the side facing the patient.

10. X-ray examination apparatus according to claim 2, characterized in that the open section (12) has a size of approximately 40×65 mm.

11. X-ray examination apparatus according to claim 9, characterized in that the open section (12) has a size of approximately 40×65 mm.

* * * * *